United States Patent
Karell

[11] Patent Number: 5,817,124
[45] Date of Patent: Oct. 6, 1998

[54] ANAL DILATOR WITH SELF-EXPANDING ELEMENT

[76] Inventor: Manuel L. Karell, 3573-22 St., San Francisco, Calif. 94114

[21] Appl. No.: 867,320

[22] Filed: Jun. 2, 1997

[51] Int. Cl.⁶ .................................................. A61M 29/00
[52] U.S. Cl. ........................... 606/197; 604/48; 604/104; 604/286
[58] Field of Search .................................. 606/191, 192, 606/193, 196, 197, 198, 199; 604/48, 104, 105, 285, 286

[56] References Cited

U.S. PATENT DOCUMENTS

| | | | |
|---|---|---|---|
| 2,290,571 | 4/1942 | Peyton | 606/197 |
| 4,467,806 | 8/1984 | Bhiwandiwala et al. | |
| 4,624,258 | 11/1986 | Stubbs | |
| 4,686,985 | 8/1987 | Lattick | |
| 4,906,239 | 3/1990 | Bruhl et al. | |
| 4,932,958 | 6/1990 | Reddy et al. | |
| 5,178,627 | 1/1993 | Hudock | 606/197 |
| 5,584,827 | 12/1996 | Korteweg et al. | |

*Primary Examiner*—Michael Powell Buiz
*Assistant Examiner*—David O. Reip

[57] ABSTRACT

An anal dilator for treating anal disorders, such as fissure-in-ano, having a self-expanding means for slowly dilating the anal muscles to cause a relaxation of anal muscles thereby promoting healing. The anal dilator comprises three sections: a first end section positioned within the rectum, a second middle section positioned within the anal sphincter muscle, and a last end section outside of the body between the buttocks. The second middle section having a self-expanding element means may be a vegetable protein, such as laminaria japonica, or a non biologic substance, such as sponge rubber. Additionally, it may also contain medications for local or systemic delivery.

10 Claims, 5 Drawing Sheets

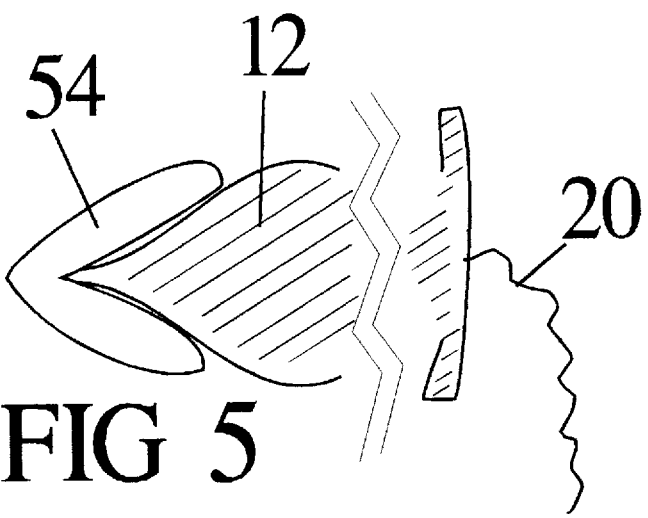
FIG 5
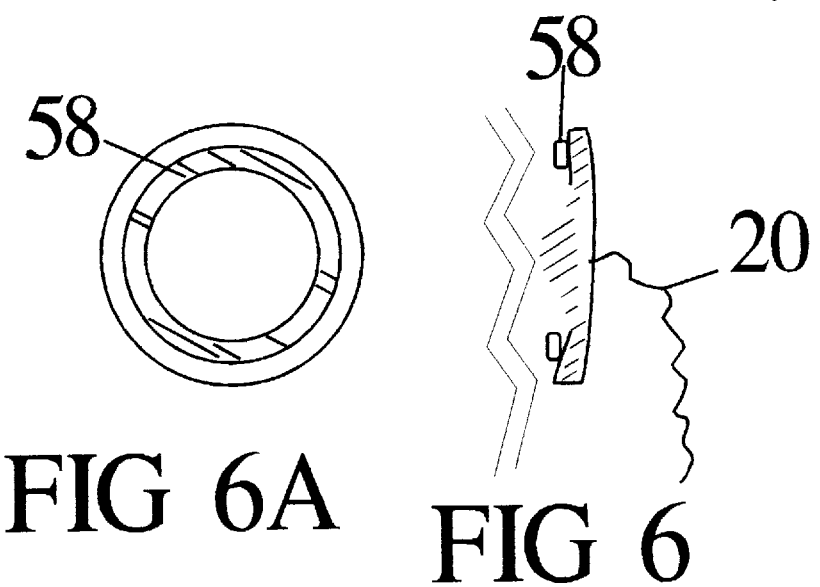
FIG 6A
FIG 6

ANAL DILATOR WITH SELF-EXPANDING ELEMENT

TECHNICAL FIELD OF THE INVENTION

The technical field of the invention is related to orifice dilators and more particular to an anal dilator for treating medical problems, such as fissure-in-ano.

BACKGROUND OF THE INVENTION

In theory, the reasons why anal fissures occur is lack of blood supply with concomitant tissue breakdown, mechanical tearing caused by fecal matter, medical conditions causing inflammation, conditions causing increased blood vessel pressure, as in pregnancy, hemorrhoids, and/or trauma.

Once a fissure (crack in mucosa) occurs, the anal muscles go into spasm, which causes a decrease in blood supply, thereby causing an increase in tissue breakdown; thus the fissure increases in size or will not heal. Muscles which are in spasm causes pain, which in turn causes more spasm. The pain associated with anal fissures can be extreme.

It has been found that dilating the anal muscles improves healing. This dilation may occur under general or local anesthesia, and with such instruments as described in referenced patents. In theory, dilation causes muscle spasm to decrease. A relaxed muscle allows for increased blood flow and enhanced healing.

Ultimately, when medical treatments fail, the anal fissure enters a chronic stage and may not heal. Surgery, a lateral sphincterotomy, (that of cutting an internal anal sphincter muscle), is the ultimate method of relaxing a muscle. It is frequently used to promote healing. Adverse problems associated with surgery include bleeding, leakage, and incontinence. It is felt that early treatment of an anal fissure can prevent entering a chronic stage.

U.S. Pat. No. 4,467,806 to Bhiwandiwala, 1984 is an osmotic cervical dilator.
U.S. Pat. No. 4,624,258 to Stubbs, 1986 is a cervical dilator.
U.S. Pat. No. 4,686,985 to Lottick, 1987 is for an anal dilator and occluder.
U.S. Pat. No. 4,906,239 to Bruhl, 1990 is a hemorrhoid treatment rod.
U.S. Pat. No. 4,932,958 to Reddy, 1990 is a prostate balloon dilator.
U.S. Pat. No. 5,584,827 to Korteweg, 1996 is a nasal packing article.

A variety of insertion and expansion elements used for orifice dilation purposes are known to the art, such as those patents reference above. The present invention overcomes the prior art by providung a means for a self-expanding anal dilator which may also deliver local or systemic medication.

The present invention overcomes the prior art by providung a means for self treatment.

The present invention provides a means for reduction of pain caused by anal fissures.

The present invention provides a means for early treatment before a chronic disorder develops.

The present invention may obviate the need for general anesthesia and surgery and their adversely created problems, such as leakage and incontinence.

SUMMARY OF THE INVENTION

A disposable self-expanding anal dilator which expands slowly over hours to stretch the anal sphincter muscle, is inserted into the rectum via the anus. It is used at the very earliest signs of a fissure-in-ano, and is inserted between defecations.

The present invention employs a device having a central sponge rubber core coated with a plant protein. It's shape comprises three sections: a section having a lubricated cone shaped front end for ease of insertion; a second middle section contains a concave region having a self-expanding means which is positioned within an anal sphincter muscle; a third section contains disc-shaped externally positioned collar having a diameter much larger than the diameter of the entrance of the anus. The collar member may be initially held in place by an adhesive, thus preventing the device from migrating inward into the anal canal and rectum. The collar means also has a string to assist in pulling and removing it from the anus.

Thus the dilator is used between defecations and is disposable.

The central core and/or the expanding element may contain medicines for local and systemic delivery.

The self-expanding means may contain a plant protein made from the root stalk of a seaweed known as laminaria japonica, which may expand as much as 300 percent on contact with body fluids. This action slowly and automatically expands the anus over a period of several hours. Pain and muscle spasm is relieved by this action.

The device may be inserted by the individual having the fissure or by his/her physician.

The device may be composed of biodegradable material for flushing down toilet drain.

DESCRIPTION OF DRAWINGS

FIG. 5 is a close up schematic representation of lubrication applied to cone shape insertion end.

FIGS. 6, 6A are close up schematic representations of an adhesive applied to collar means.

DETAILED DESCRIPTION OF THE PREFERRED FORM OF THE INVENTION

Figure 1:
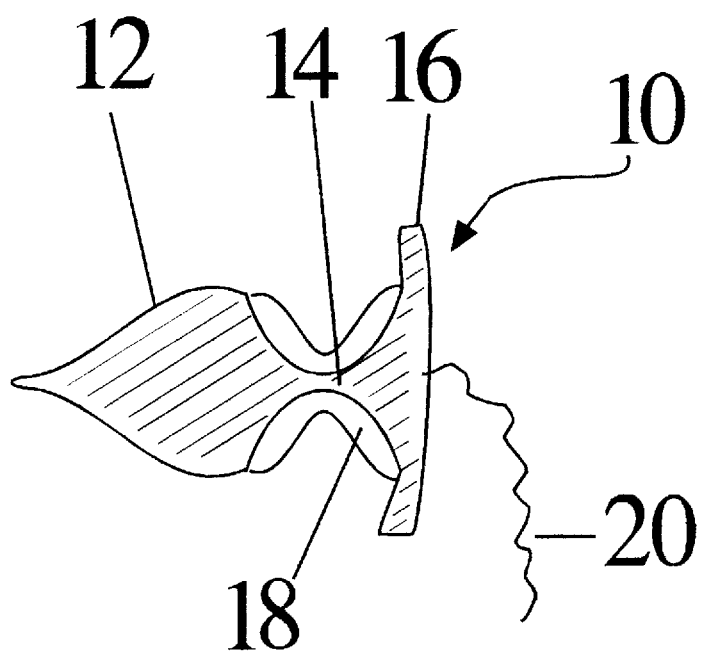
FIG. 1 is a schematic drawing of an anal dilator embodying the concepts of the present invention having an inserting end, a middle concavity means surrounded by a self-expanding element means, and a collar means affixed with a grippable means.
Figure 2:
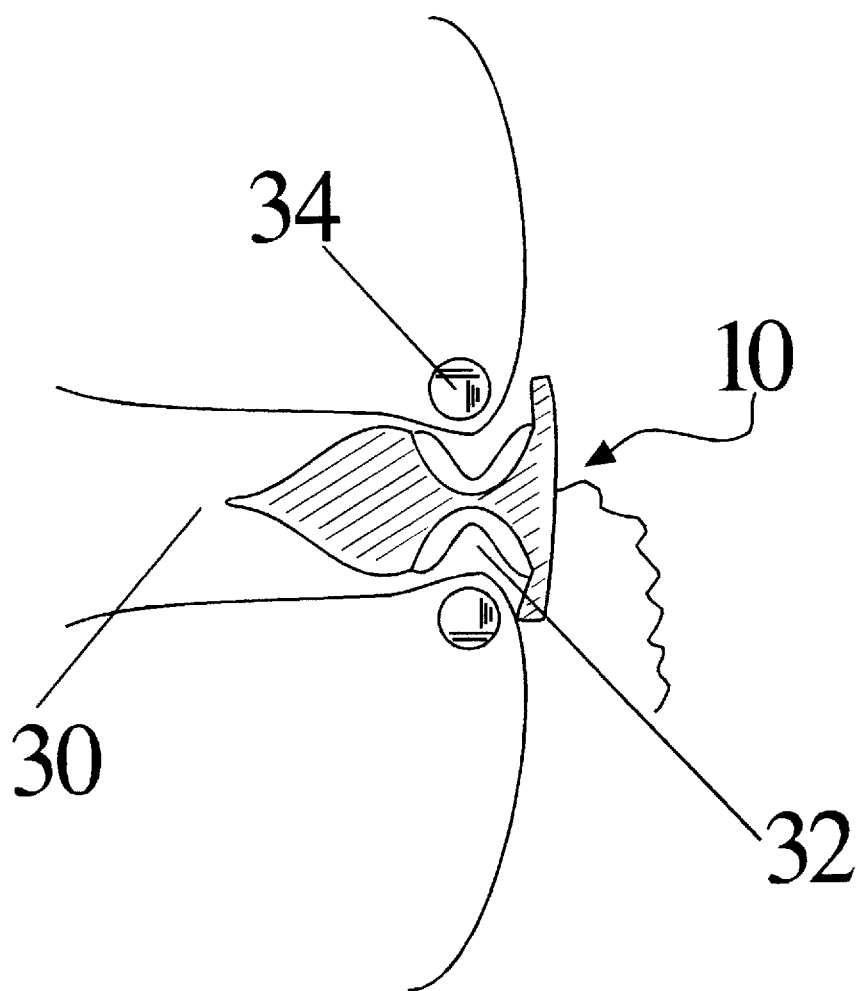
FIG. 2 shows a schematic drawing of an anal dilator positioned within a rectum and anus while having a collar section resting between buttocks external to the anus.

The present invention is disclosed in FIGS. 1–6 wherein in FIG. 1 there is a preferred embodiment of a device(10) comprising three sections: a first end region, a middle region and a last end region. The first end region comprises a cone shape(12) for easy insertion into a rectum through an anus. The cone shape(12) is contiguous to a middle region concavity(14) for fitting, as is seen in FIG. 2, within an anus(32) within an anal sphincter muscle(34) and into a rectum(30). The concavity(14) is contiguous to a last end region collar means(16), which is disc-shaped as is best seen in FIGS. 6 and 6A. The collar means(16) remains external to the body, as depicted in FIG. 2, and is sufficiently large to prevent migration of said device(10) into the rectum through the anus.

Figure 3:
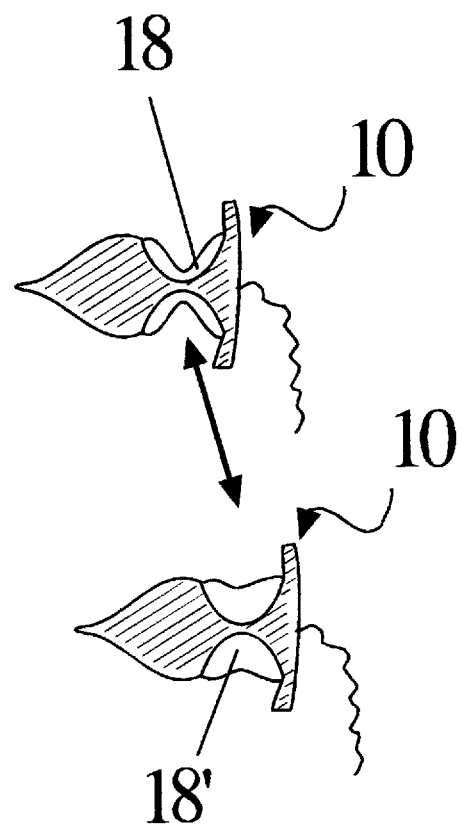
FIG. 3 shows the self-expanding element means going from the un-expanded to the expanded condition.

The concavity means(14) is surrounded by a self-expansion element means(18), which radially expands(18') as seen in FIG. 3, on contact with rectal and anal fluids. This action slowly and automatically expands the anus over a period of several hours. Pain and muscle spasm is relieved by this action.

The collar means(16) has a grippable means(20) affixed, such as a string. After having dilated, the device is extracted by pulling on string(20) for disposal.

Additionally, as is seen in FIGS. 6 and 6A, the leading edge of said disc-shaped collar means(16) may have an adhesive(58) to assist in maintaining device(10) positioned within an anal sphincter muscle while dilation occurs.

Figure 4:
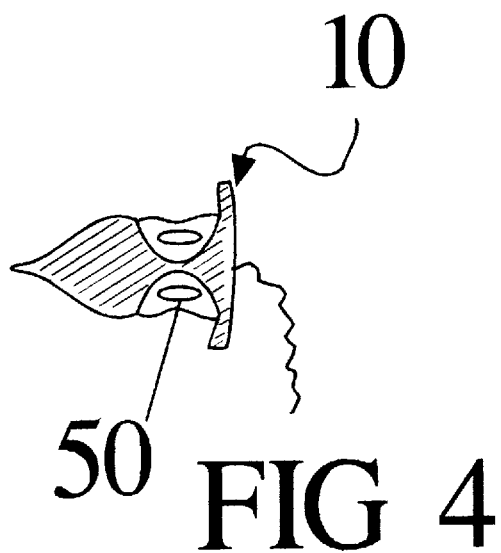
FIG. 4 is a close up schematic representation of a medication delivery means within self-expanding element means.
Figure 4A:
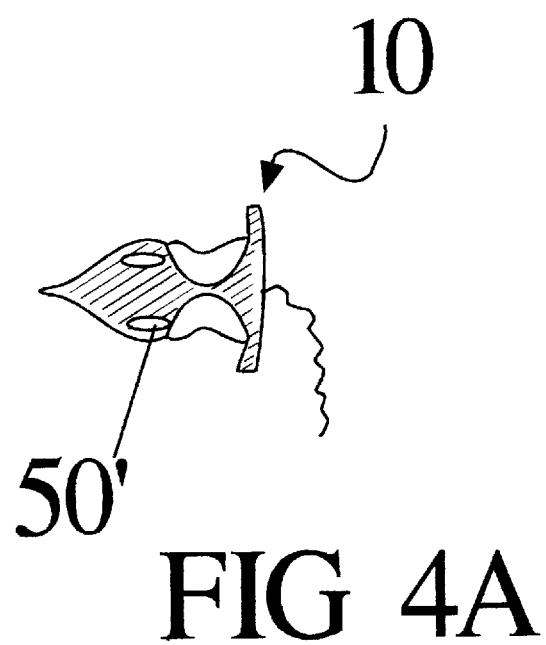
FIG. 4A is a close up schematic representation of a medication delivery means not within expanding element means.

FIG. 4 shows a device(10) additionally having a medication dispensing means(50) within said self-expansion element means. Alternatively, as is seen in FIG. 4A, the medication dispensing means(50') is not within said self-expansion element means. Medication dispensing means are well known in the art and in public documents and therefore are not further described.

FIG. 5 shows said cone shape(12) additionally having a lubrication means(54) for decreasing friction during insertion.

While the use of an anal dilator with a self-expansion element means is novel, and the above description contains many specificities, these should not be considered as limitations on the scope of invention, but rather as exemplification's of preferred embodiments thereof. It is intended that the invention not be limited to a particular embodiment disclosed as the best mode contemplated for carrying out the invention, but that the broadest aspects of the invention will include all embodiments and equivalents falling within the scope of the general principles disclosed herein. Thus, the principles of the present invention may be applied to similarly expandable anal dilator elements other than those described such as polyvinyl alcohol sponge, polyurethane sponge, silicone sponge, collagen sponge, or other material, such as spring metal used in stents.

I claim:

1. An anal dilator comprising:
    a generally cylinder-shaped device configured for insertion through an anus into a rectum, said device comprising three contiguous regions, including a first end region which is adapted for insertion into the rectum, a middle region which is adapted for positioning within and for dilating an anal sphincter muscle, and a last end region which is adapted to be outside of the body between the buttocks for preventing migration of said device through the anus and into the rectum;
    wherein said device further comprises self-expansion element means, said self-expansion element means comprising a biologic material having the property of undergoing substantial radial self-expansion by contact with fluids normally present within the rectum and anus.

2. A device of claim 1 wherein said first end region comprises a cone-shaped means for enhancing ease of insertion; and wherein said middle region comprises a concavity means for enhancing positioning wherein said concavity means is surrounded by said self-expansion element means; and wherein said last end region comprises a disc-shaped collar means having an adequately large diameter to impede migration.

3. A device of claim 2 additionally having a hand grippable means operatively affixed to said collar means for allowing a pulling force to be applied directly to said collar means so as to withdraw said device from the rectum and anus.

4. A device of claim 2 wherein additionally said cone-shaped means is lubricated for decreasing insertion friction.

5. A device of claim 2 additionally having said collar means comprising an adhesive means for adhering said collar to skin surrounding the anus.

6. A device of claim 1 wherein said self-expansion element means is biologic material having the property of undergoing substantial radial expansion when in contact with fluids normally present within the rectum and anus.

7. A device of claim 5, wherein said self-expansion element means comprises a vegetable protein.

8. A device of claim 1 additionally having a medication dispensing means for dispensing a medicine while within the rectum and anus.

9. A device of claim 8 wherein said medication dispensing means is operatively within said self-expansion element means.

10. A device of claim 8 wherein said medication dispensing means is not within said self-expansion element means.

* * * * *